United States Patent [19]
Klaassen et al.

[11] Patent Number: 6,050,821
[45] Date of Patent: Apr. 18, 2000

[54] ULTRASONIC METHOD AND APPARATUS FOR CREATING DENTAL IMPRESSIONS

[75] Inventors: Richard E. Klaassen, West Chester; Herbert A. Asch, Cincinnati, both of Ohio

[73] Assignee: Asch-Klaassen Sonics, Inc., Cincinnati, Ohio

[21] Appl. No.: 09/371,366

[22] Filed: Aug. 10, 1999

Related U.S. Application Data

[60] Provisional application No. 60/096,349, Aug. 13, 1998.

[51] Int. Cl.⁷ .............................. A61C 9/00; A61C 19/04
[52] U.S. Cl. ............................................................. 433/214
[58] Field of Search ................................ 433/214, 72, 29, 433/68, 69, 213; 356/376

[56] References Cited

U.S. PATENT DOCUMENTS

| | | | |
|---|---|---|---|
| 5,440,393 | 8/1995 | Wenz | 356/376 |
| 5,570,182 | 10/1996 | Nathel et al. | 356/345 |
| 5,755,571 | 5/1998 | Companion | 433/72 |

*Primary Examiner*—Nicholas D. Lucchesi
*Attorney, Agent, or Firm*—Neal O. Willmann

[57] ABSTRACT

This disclosure relates to a method and apparatus for mapping the structure and topography of dental formations such as peridontium and teeth, both intact and prepared, for diagnosis and dental prosthetics and bridgework by using an ultrasonic scanning technique. This method can provide highly resolved details of orally situated dental formations thus enabling diagnosis and the preparation of precision moldings and fabrications that will provide greater comfort and longer wear to the dental patient.

2 Claims, 2 Drawing Sheets

ULTRASONIC METHOD AND APPARATUS FOR CREATING DENTAL IMPRESSIONS

CROSS REFERENCE TO A RELATED APPLICATION

This application claims the benefit of U.S. Provisional application No. 60/096,349 filed Aug. 13, 1998.

BACKGROUND OF THE INVENTION

To make an impression of a dental structure, a modeling procedure is typically employed. Traditionally, impressions have been made with wax, plaster reversible and irreversible hydrocollids and elastomeric or rubber-like materials. The impression materials are placed in the mouth around the dental structure to be modeled and allowed to cure. Currently, the preferred procedure for preparing an impression of a dental structure is to employ a self-setting elastomeric polymer. This polymer is introduced into the mouth of the dental patient and applied to the surface of the formation to be modeled. The polymer is allowed to harden or cure, an impression is formed, then removed and sent to a dental lab where it is used as a mold for the prosthetic device. The impression is the negative image for the preparation of the positive model.

This technique has several drawbacks: Typically, the materials work best in a dry field, since the mouth is wet, a dry field is difficult to obtain Foreign material, temperature, humidity, poor fill, patient movement and practitioner error all contribute to inadequate impressions. Furthermore, once a conventional impression is made, it can only be used once, and occasionally twice, before details are compromised, damaged or distorted, thus limiting multiple uses.

Another consideration in the conventional casting process is the time lost in physically sending the impression to the laboratory. Shipment necessarily increases the inconvenience for the patient who, in most instances, will endure the discomfort of a temporary prosthesis and perhaps even experience a change in oral features if the transit and laboratory times are particularly protracted.

DESCRIPTION OF THE PRIOR ART

Techniques employing waves and energies have been used to offer some alternatives to the mold casting procedure. An infra-red cad-cam has been used to map oral structures and make single-tooth prosthetics. Because this infra-red technique can create a digital representation of the structure, it offers the advantage of creating an "impression" that is immediately transmittable from the subject to the dental laboratory. This digital transmission will diminish inconvenience for the patient and eliminate the risk of damage to the mold. However, because of interference from foreign material such as blood and saliva, this infra-red mapping technique cannot be used in the mouth.

Ultrasonic probes are currently being used in some dental applications. Most relevant of the patent references in the prior art is U.S. Pat. No. 5,100,318, which issued Mar. 31, 1992 to Demyun et al. That document describes a method and probe device for measuring the depth of periodontal pockets from the gum surface adjacent a tooth to the bone surface at the bottom of the pocket thus providing a diagnosis of the gum and, ultimately, and a prognosis for the dental condition in the mouth.

SUMMARY OF THE INVENTION

In view of the methods and techniques previously employed for creating impressions of oral structures, the use of ultrasound to map and thus permit the creation of highly resolved models of the oral structure appears to be a significant departure from the prior art. Accordingly then, the present invention can be summarized as follows: A method for mapping the surface of a dental structure within an oral cavity, said method comprising: a) providing a transducer array movably positioned to produce an outgoing fixed ultrasonic pulse for impinging all aspects of the exposed surface of said dental structure thereby establishing an ultrasound pulse travel path having a variable reflected delay time; b) measuring the difference between said fixed outgoing ultrasonic pulse and the variable reflected delay time of an ultrasonic echo pulse signal reflected from said dental structure; and c) displaying a representation of said difference between the fixed excitation time pulse and the variable, reflected delay time to depict the surface contour of said dental structure.

This disclosure also includes the apparatus for mapping the surface of a dental structure within the oral cavity, said apparatus comprising: a) a transducer array consisting of a plurality of transducers for emitting and detecting ultrasonic pulses including reflected ultrasonic pulse echoes; b) a housing means to contain and guide motion of the transducer array; c) an articulating means for exposing said transducer array over and around all aspects of said dental structure; d) an electric power source for exciting said transducer array; e) a power source for activating the movement of the articulating means; f) an amplification means for enhancing said ultrasonic pulse echoes; and g) a computing means for converting said ultrasonic echo pulse signals into interpretable recreations.

Ultrasound (ultrasonic impression technique) has both clinical and diagnostic applications. For example, clinically, the mouth can be mapped to produce models of occlusal surfaces for study and examination to determine abnormal wear and articulation. Models of the teeth and gingiva can be made to provide for the improved construction of dentures, full and partial, crowns and bridges. The periodontium can be measured with comparisons made over time to determine periodontal changes and aid in the diagnosis of periodontal disease.

Ultrasonic mapping can also enhance endodontic procedures. By rotating an ultrasonic probe in the canal of a tooth, "visualization" of the canal and soft tissues can be obtained. Efficient debridement can be achieved by increasing the frequency of ultrasound to remove soft tissue from the canal.

As a diagnostic aid, ultrasonic examination can be used to compare and check the effectiveness of standard techniques such as color flow Doppler tests that are conducted to determine blood flow to and in the tooth.

Cracks and carries can be detected by the disclosed method, and the gingiva and contour or bone surrounding the teeth can be measured by modulating the ultrasonic frequency to achieve automated periodontal charting. Used in this way, diagnosis by ultrasound can create very precise computerized records. In addition, ultrasound can be used with x-rays or replace them if x-rays are contraindicated.

While eliminating the problems inherent in traditional impression techniques, ultrasound impressions of oral structures will also provide more accuracy and reliability in the preparation of prosthetic models. Ultrasound can work in a wet environment detecting cracks, voids and carries and therefore it has application in diagnostic as well as in prosthetic techniques. In conjunction with appropriate computer software, models can be constructed from the ultrasound "impression" thus permitting a model to be created with a high degree of accuracy and reliability. Additionally, the computerized impression can be sent digitally to the dental lab where it can be processed and examined before and after prosthetic procedures are performed permitting an opportunity for dialog between the dentist and technician thus increasing the likelihood of preparing the best possible prosthesis. Information can also be sent to insurance companies to facilitate processing of dental claims and to other professionals for purposes of consultation.

DESCRIPTION OF THE PREFERRED EMBODIMENTS

Figure 1:
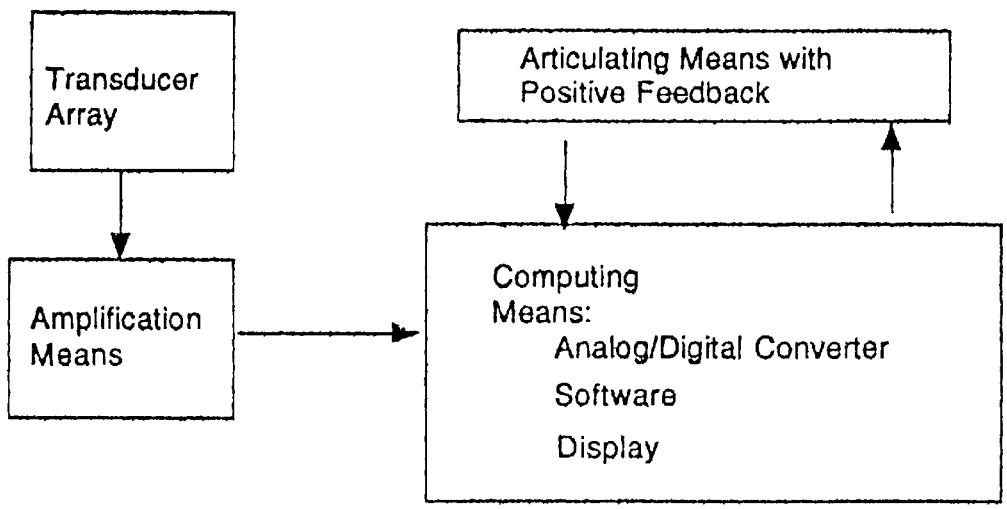
FIG. 1 is a schematic block diagram of the instrumentation of an ultrasonic mapping apparatus.

A general understanding and appreciation of the disclosed method and apparatus will be facilitated by referring initially to FIG. 1, a block or schematic diagram depicting the instrumentation employed in a preferred embodiment.

Included in the instrumentation, of course, is the sensor or transducer array providing a plurality of transducers which will both emit and receive ultrasonic wave activity. On electrical excitation, the transducer will emit an outgoing ultrasonic pulse which, in this instance, if aimed correctly, will impinge on the surface of the dental structure(s) to be mapped or studied. The outgoing or emitted pulse, after contacting the surface of the dental structure being studied, will be reflected from the surface of the structure and create an echo pulse which will be detected by the transducer array. This reflected echo pulse signal will then be amplified by an amplification means and sent to an analog/digital converter which is part of the computing means for comparison with the emitting pulse. By converting the reflected pulse signal to a digital code and then comparing it with the code of the emitted signal, software in the computing means can recreate and display a topographical depiction of the surface of the structure being studied.

Figure 2:
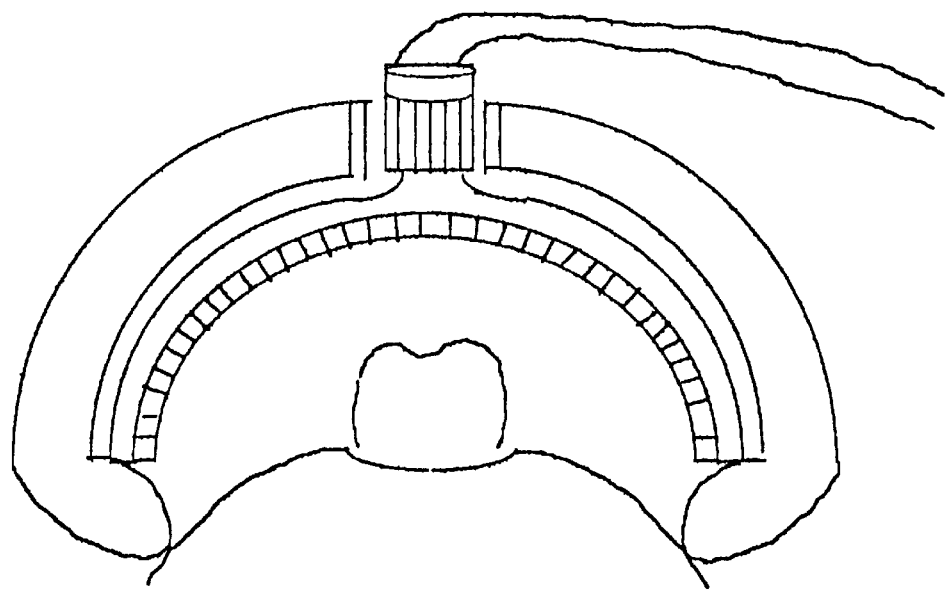
FIG. 2 is an axial cross-section view of the sensor array of the disclosed ultrasonic mapping apparatus within its housing.

For further understanding of the method and apparatus disclosed herein, please refer to FIG. 2. Bear in mind that the oral structure to be studied will typically be a relatively inaccessible tooth, and more particularly it frequently will be a prepared tooth awaiting the fitting of a crown. In the actual practice of the invention, an arc-shaped, linear array of ultrasonic sensors is rotated around and over the prepared tooth. Referring to FIG. 2, it will be apparent that in a preferred embodiment the sensor array, which is typically a plurality of transducers, are positioned on a rotating arc within a shell which acts as the housing for the array. The housing and swinging arc can be structurally compared to an ice cream scoop with a lever activated arc for separating the ice cream from the bowl of the scoop. The bowl of the scoop is comparable to the housing of the apparatus and the lever activated arc is comparable to the sensor or transducer array.

The primary function of the housing is to contain and guide motion of the transducer array, and, in a preferred embodiment, the housing will be designed to be situated over all of the exposed tooth to be studied; and, where necessary, the housing will also serve to confine a liquid couplant.

In order to fit snugly over the tooth to be mapped, the open rim of the housing will be fitted with a gasket of soft, deformable material. It will be developed to fit on the gum and around the tooth. It is desirable for the gasket to be relatively water tight to contain the couplant. When the housing is securely in place, a drive mechanism situated in the housing and in electrical communication with the sensor array, can be activated to swing the sensor array in an arc, usually about 150°, over and around the tooth. While articulating in this fashion, the transducers on the articulating arc, can be electronically activated to vibrate and emit ultrasonic pulses, some of which will strike the exposed surface of the tooth and be ricocheted to or be reflected to other transducers on the arcing sensor array. These echo or reflected pulse signals, after being detected by transducers on the array, can be collected, analyzed and compared to produce a recreation of the tooth or dental structure being examined.

To recap, somewhat, when electrically activated, the transducer will vibrate and create sound waves which will travel from the sensor array through the liquid couplant to the surface of the prepared tooth. The sound waves are reflected, creating echo pulses, back to the array of transducers and "detected". The sensor will "detect" the echo signal. The echo signal is converted to an electrical signal, which is amplified, digitized and downloaded to a computer containing software capable of analyzing the digitized signal. By collecting reflected or scattered signals form as many angles as possible, the computer will have sufficient time-of-flight measurements to perform a tomographic computation to model or map the prepared surface.

As indicated previously, a prototypical sensor array has been designed and will be constructed to resemble an ice cream scoop with a swinging arc. It has 150° with 128 sensor elements in a 1 cm diameter. Each element is 0.1 mm when situated radially and 2 mm when situated axially. The sensor elements have been designed to a broadband sound pulse with a center frequency in the range of 10–20 MHz, with a sound absorbing material bonded on the back side. From the prototype it has been observed that the size, shape and arrangement of the sensor elements could vary considerably from those currently employed. Furthermore, altering the combination of wavelength and axial focus can affect and fine-tune the resolution desired.

The shell with the semicircular array of sensor elements arranged on the arc within the "scoop" is placed over the prepared tooth. Because of the innovative arrangement of the sensors, teeth in both the upper and lower jaws are equally accessible to scanning. The arc of transducer sensor elements is then rotated over and around the prepared tooth as it rotates 150° within the hemispherical shell acquiring a set of signals from the scattered waves at preselected intervals. The intervals are selected to achieve the desired image resolution and can be as numerous as necessary within practical limits, or even eliminated to the point of receiving continuous scattered signals. The ultrasonic pulses emanating from the emitter are generated in response to a positional indicator encoded within the shell; and they can be controlled from a rheostat on the drive mechanism and even further controlled from a timing circuit for an array moving at a predetermined speed.

The drive mechanism is contained within the shell to minimize patient discomfort and is typically a spring-loaded cable but could just as easily be electronic. A hydraulic drive mechanism has certain advantages: The drive fluid could conveniently be water at low pressure and could also be the same liquid as the couplant.

The couplant occupies the space between the shell and the prepared tooth. The couplant is ideally contained within the shell by a circumferential seal; or alternatively, containment is ignored and disregarded by providing a constant, laminar flow into the shell and thus continuously surrounding the prepared tooth.

Figure 3:
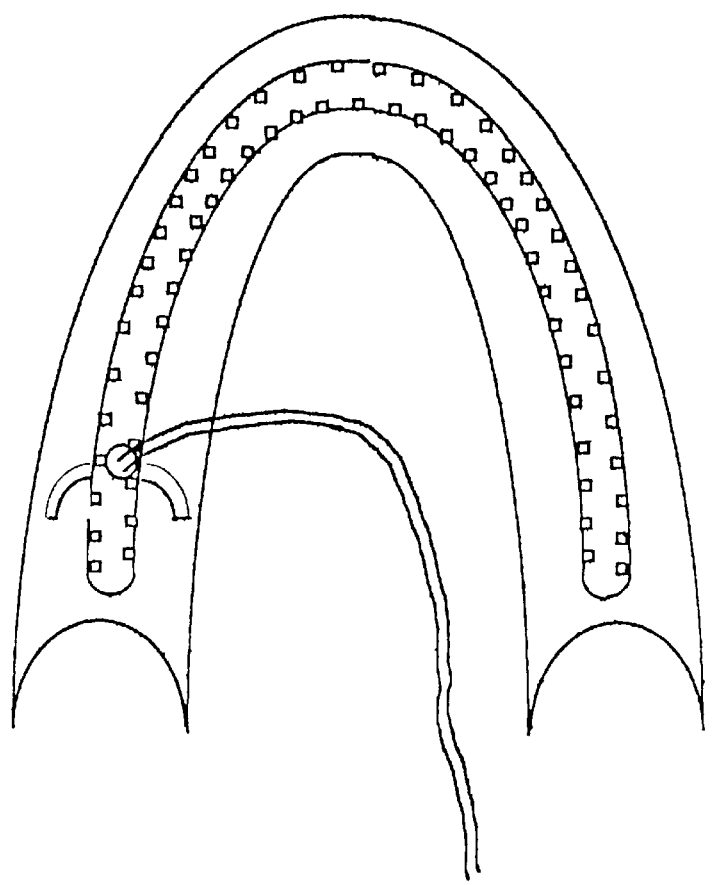
FIG. 3 is a partially transparent schematic for an ultrasound mapping apparatus for all structures in a jaw.

Other embodiments of the housing and sensor array can be arranged to perform other mapping tasks within the oral cavity. For instance, FIG. 3 depicts a partially transparent schematic representation of a housing and sensor array combination that would be suitable for mapping all structures within either an upper or lower jaw. In this embodiment, instead of arcing over and around each tooth, the sensor array can be driven over and around all the teeth in the jaw. This accomplished by having an arched housing in a U-shape containing a transducer array formed into a 180° arc attached to a drive mechanism capable of moving the array over and around all teeth in the jaw. Any of a variety of drive mechanisms could be used including teeth 11 and gear or drive screws.

Figure 4:
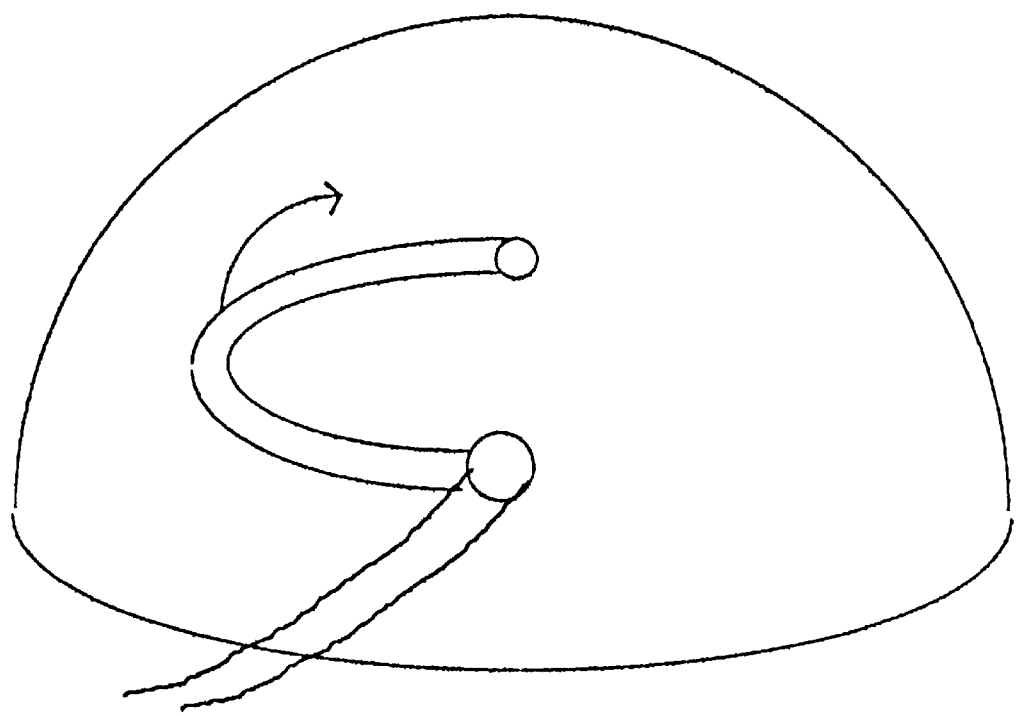
FIG. 4 is a transparent schematic showing the housing of an ultrasound mapping apparatus with a pivoting articulating means for the sensor array.

In FIG. 4, an alternative embodiment of the transducer array is depicted. Here the housing and transducer array are similar to the design arrangement found in FIG. 2, but in this instance the transducer array is driven by a pivoting drive mechanism. Such an arrangement will enable the transducer array to move with greater maneuverability thus permitting more resolutions and a finer recreation of the oral structure.

The transducer array is typically located in a position proximal to where the data are to be acquired, and a trigger pulse initiates the sequence of data collection. Although the transducer elements (sensors) could be activated simultaneously and receive signals sorted by frequency, crosstalk between elements is eliminated by triggering the sensors one at a time. The element then waits for a return echo which is converted into a measurable signal. And although only one sensor is triggered at a time, all sensors are monitored simultaneously to maximize the amount of information recorded over and around the reflecting surface of the prepared tooth. It is beneficial to monitor echo signals with all sensors because the irregular geometric features of the prepared tooth will scatter sound in all directions.

The echoes received are transmitted through a cable to an electronic receiver positioned near the patient. The echoes are analyzed individually or as a tomographic reconstruction of the time-of-flight data to procure a two-dimensional view of the prepared tooth. These two-dimensional depiction's are known as vertical slices. They can be combined with other vertical slices to form a three-dimensional phased tomographic reconstruction and a three-dimensional view of the dental structure being examined.

The acquired data can be stored as either as the reconstructed signal or as raw data. In the unreconstructed form, the data can be transmitted to a lab where it can be used to construct a physical mold.

We claim:

1. A method for mapping the surface of a dental structure within the oral cavity, said method comprising:

a) providing a transducer means positioned to produce a fixed, outgoing ultrasonic pulse for impinging directly on said dental structure surface thereby establishing an ultrasound pulse travel path having a variable, reflected delay time;

b) measuring the difference between said fixed, outgoing pulse and the variable delay time of an ultrasonic echo pulse signal reflected from the dental structure surface; and c) displaying a representation of said difference between the fixed pulse time and variable reflected delay time to depict the surface contour of said dental structure.

2. An apparatus for mapping the surface of a dental structure within the oral cavity, said apparatus comprising:

a) a transducer array consisting of a plurality of transducers for emitting and detecting ultrasonic pulses, including reflected echoes;

b) a housing means to enclose and guide said transducer array over and around said dental structure;

c) articulating means for exposing said transducer array to all aspects of the surface of said dental structure;

d) an electrical power source for exciting said transducer array;

e) a power source for activating the movement of said articulating means;

f) an amplification means for enhancing said ultrasonic echo pulse signals; and g) a computing means for converting said ultrasonic echo pulse signals into an interpretable recreation.

* * * * *